United States Patent [19]

Moser

[11] Patent Number: Plant 6,799

[45] Date of Patent: May 16, 1989

[54] HIBISCUS PLANT NAMED LAVA

[75] Inventor: Frank C. Moser, Alva, Fla.

[73] Assignee: Yoder Brothers, Inc., Barberton, Ohio

[21] Appl. No.: 52,417

[22] Filed: May 21, 1987

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Hibiscus plant named Lava particularly characterized by its bright orange flower color, regular flower form, small to medium sized leaves with a serrated margin, vigorous upright growth, excellent branching action, single day flower life, good low light bud initiation, and ease of rooting cuttings.

3 Drawing Sheets

The present invention comprises a new and distinct cultivar of Hibiscus, botanically known as *Hibiscus Rosa-sinensis L.*, and referred to by the cultivar named Lava.

Lava, identified as 83026015 during the breeding and selection process, originated from a planned cross hybridization between two selected breeding lines in a controlled breeding program in Fort Myers, Fla. by Frank C. Moser.

The female or seed parent is an unnamed cultivar designated as code #0005 and the pollen or male parent is an unnamed cultivar designated as code #0002.

Lava was discovered and selected as a flowering plant within the progeny of the stated cross by Frank C. Moser in October 1983, outside in ground beds in Fort Myers, Fla.

The first asexual reproduction of Lava was accomplished when vegetative cuttings were taken from the initial plant selection in November of 1983 in Fort Myers, Fla. from plants grown outside in ground beds, by technicians working under formulations established and supervised by Frank C. Moser.

Horticultural examinations of controlled flowerings of successive generations of plants derived from cuttings taken from the original selection have shown that the unique combination of characteristics as herein disclosed for Lava are fixed and retained through successive generations of asexual reproduction.

Lava has not been observed under all possible environmental conditions. The phenotype may vary significantly with variation in environment such as temperature and light intensity.

The following observations, measurements and comparisons describe plants that were grown in Fort Myers, Fla. in a controlled greenhouse environment and following a commercial schedule.

The following traits have been repeatedly observed and are determined to be basic characteristics of Lava, which, in combination, distinguish this Hibiscus as a new and distinct cultivar:

1. Bright orange flower color.
2. Regular single flower form.
3. Small to medium sized leaves, with serrated margins.
4. Vigorous upright growth.
5. Excellent branching habit.
6. Flower life is a single day.
7. Good low light bud initiation.

8. Easy to root.

The accompanying photographic drawings show typical plant habit, and flower and leaf characteristics of Lava, with colors being as nearly true as possible with illustrations of this type.

Sheet 1 is a color photograph of Lava grown as a commercially finished pot plant.

Sheet 2 is a color photograph illustrating the distinctive characteristics of the upper and lower surfaces of the flower.

Sheet 3 is a color photograph showing the variation in leaf shape that can characteristically be found on any one plant of Lava.

Of the commercial cultivars known to the inventor, the most similar in comparison to Lava is the cultivar Moesiana. Lava is similar to Moesiana in that both cultivars have vigorous growth, branch profusely, are easily rooted, have good low light bud initiation and are very floriferous.

Lava differs from Moesiana in that its flowers are a bright orange color while Moesiana bears a scarlet flower. Lava is much more resistant to bacterial leaf spot and has more sturdy branches. Also, the leaves of Lava are not as deeply cut as those in Moesiana.

In the following description, color references are made to The Royal Horticultural Society Colour Chart. The color readings were taken from greenhouse grown plants on Jan. 28, 1987. All readings were taken in an office under cool white florescent lights, facing a west window between the hours of 10:00 a.m. and 2:00 p.m.

Classification:

*Botanical.*—*Hibiscus Rosa-sinensis L.* cv. Vista.
*Commercial.*—Greenhouse pot crop.

INFLORESCENCE

A. Flower (general):
*Size.*—Medium, 11.5 cm.
*Borne.*—In axils of leaves, 1 per node.
*Form.*—Regular single.
*Life.*—1 day.
*Fragrance.*—None.
*Blooming habit.*—Continuously, year round.

B. Corolla (petals):
*Texture.*—Smooth, veins slightly raised up.
*Substance.*—Medium thick.
*Shape.*—Rounded.

*Color (fully open).*—Upper surface: base color dark orange 33A; eye, red 45B. Lower surface: predominantly dark orange 33A.

C. Bud (1 day prior to opening):
*Size.*—7 cm in length.
*Shape.*—Cigar shaped.
*Color.*—Orange red 34A.

D. Calyx: Cup shaped, 5 pointed lobes, a single prominent midvein per lobe, membranous.
*Length.*—3 cm.
*Color.*—Light green 144B.

E. Epicalyx: 6–8 pointed, narrow, sword-shaped bracts.
*Length.*—2 cm.
*Color.*—Green 137C.

F. Peduncle:
*Length.*—5–8 cm.
*Strength.*—Medium.
*Aspect.*—Smooth.
*Color.*—Yellowish green 143C.

G. Reproductive organs:
(1) *Androecium (stamens).*—Anthers: Numerous, Color (undehicsed) peach 37A. Filaments: Length 8 mm, Dark orange 33A. Pollen: Abundant, Color dark yellow 17A. Staminal column: Length 8 cm, Color orange 30A, Upper 25% antheriferous.
(2) *Gynoecium (pistil).*—Stigma: 5 in number, rounded, discoid, hairy. Color: Red 45B, diameter 2 mm. Style: Length 9 cm, Color red 45B.

Branches: 5 in number, Color white. Ovary: Rounded, Color yellowish green 150C.

PLANT CHARACTERISTICS

A. Foliage:
*Arrangement.*—Alternate.
*Shape.*—Juvenile: Heterophyllus. Mature: Entire, cordate, serrated edge. Color: Dark green 139A.
*Petiole.*—Length 3.5–4.5 cm, Aspect smooth. Color: Green 137B.
*Stipules.*—2 per node, Shape acicular (needle shaped). Color: Green 137A.

B. Stems: Aspect smooth, becoming woody with age.
C. Plant habit: Upright.
D. Breaking action: Excellent.
E. Rooting: Good.
F. Growth regulator: Required, due to vigorous growth.
G. Low light bud initiation: Good.
H. Shipping tolerance: Good.

I claim:

1. A new and distinct cultivar of *Hibiscus Rosa-sinensis* named Lava, as described and illustrated, and particularly characterized as to uniqueness by the combined characteristics of bright orange flower color, regular flower forms, small to medium sized leaves with a serrated margin, vigorous upright growth, excellent branching action, single day flower life, good low light bud initiation, and ease of rooting cuttings.

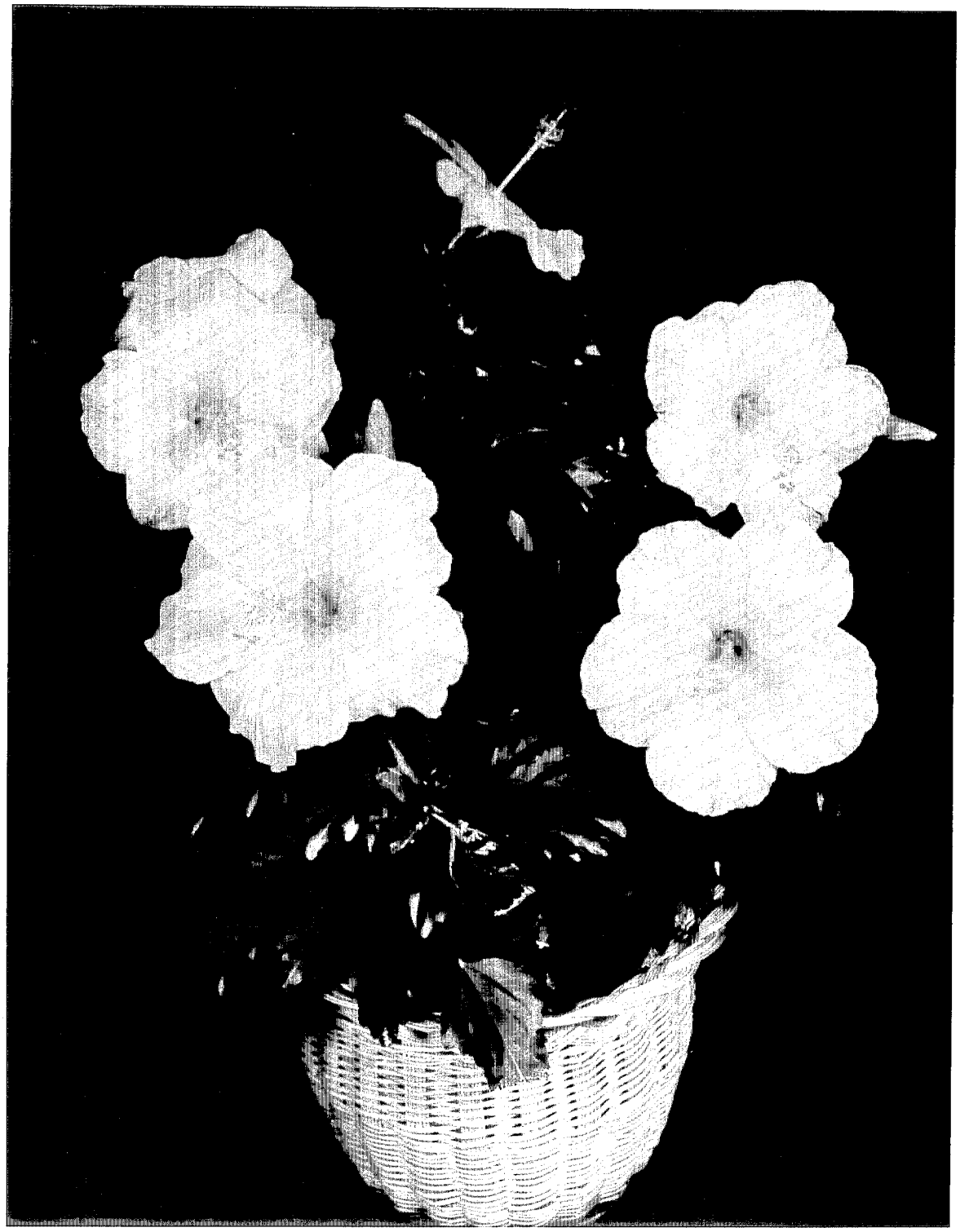

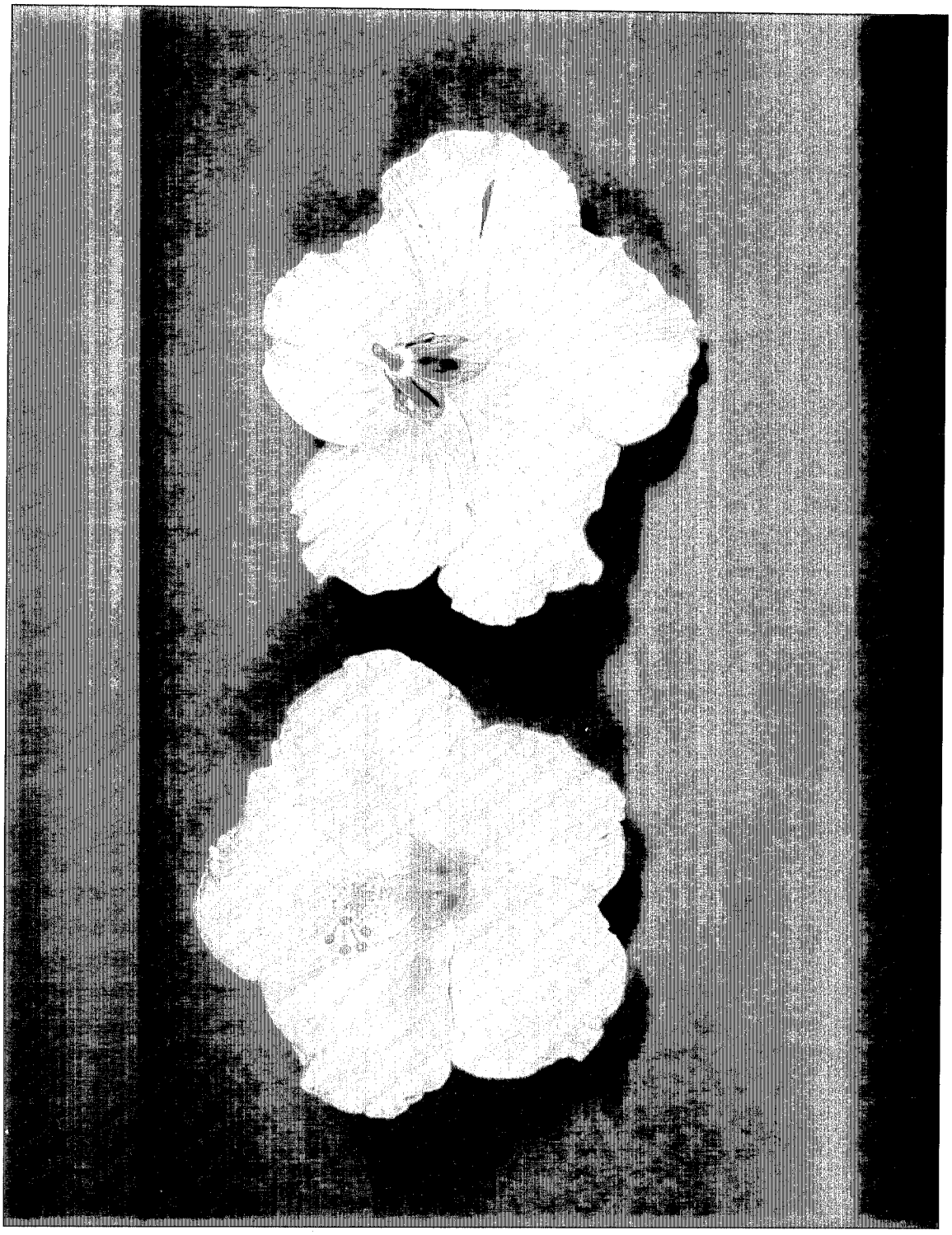

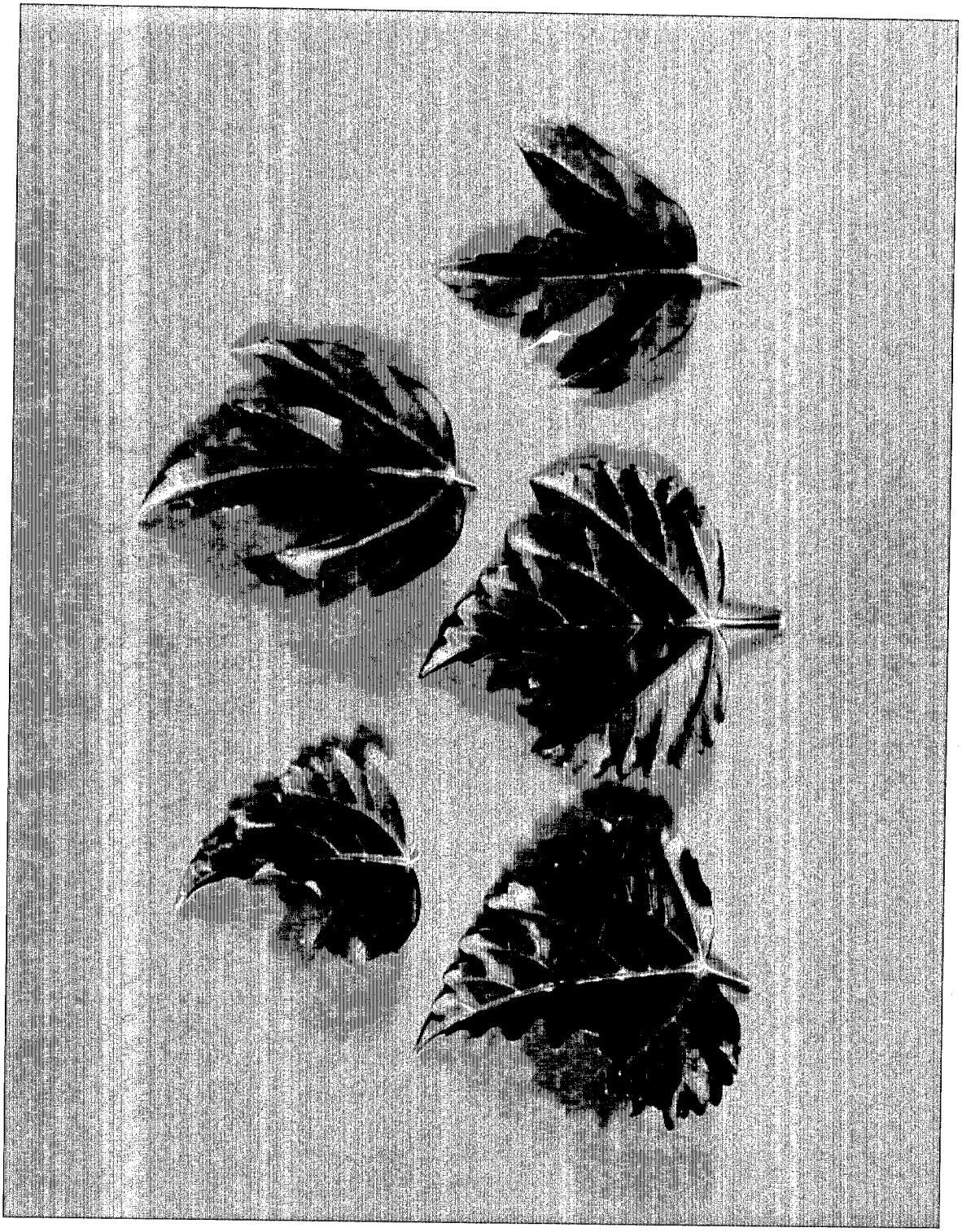

* * * * *